United States Patent [19]
Muller et al.

[11] Patent Number: 6,166,012
[45] Date of Patent: Dec. 26, 2000

[54] ANTIBIOTIC COMPOSITIONS AND METHOD FOR USING SAME

[75] Inventors: Christopher A. Muller, Foothill Ranch; Elizabeth A. Bancroft, Irvine; Janet K. Cheetham, Laguna Niguel; Harold G. Jensen, Lake Forest; Teresa H. Kuan, Placentia; David F. Power, Trabuco Canyon; Kevin D. Skule, Rancho Santa Margarita, all of Calif.

[73] Assignee: Allergan Sales, Inc., Irvine, Calif.

[21] Appl. No.: 09/365,291

[22] Filed: Jul. 30, 1999

[51] Int. Cl.[7] .......................... A61K 31/535; A61K 31/50
[52] U.S. Cl. ...................... 514/235.5; 514/250; 514/912
[58] Field of Search ................................. 514/250, 235.5, 514/912

[56] References Cited

U.S. PATENT DOCUMENTS

| | | |
|---|---|---|
| 4,382,892 | 5/1983 | Hayakawa et al. . |
| 4,454,151 | 6/1984 | Waterbury . |
| 4,551,456 | 11/1985 | Katz . |
| 5,110,493 | 5/1992 | Cherng-Chyi et al. . |
| 5,414,011 | 5/1995 | Fu et al. . |
| 5,474,764 | 12/1995 | Patel et al. . |

OTHER PUBLICATIONS

The Pharamacological Basis of Therapeutics, Gilman et al, pp. 1057–1061, 1990.

*Primary Examiner*—Zohreh Fay
*Attorney, Agent, or Firm*—Stout, Uxa, Buyan & Mullins, LLP; Frank J. Uxa

[57] ABSTRACT

Compositions including a quinolone component in an amount effective as an antibiotic when the composition is placed in a mammalian eye, and a carrier component in an amount effective to act as a carrier for the quinolone component are provided. The present compositions are substantially free of other components effective as preservatives. Preferably the quinolone component has fungistatic activity. In one very useful embodiment, the compositions include a NSAID component in an amount effective to reduce inflammation or pain when the composition is placed in a mammalian eye. Methods of using the present compositions, for example, to resolve microbial infections and/or to reduce inflammation and/or pain in a mammalian eye are included within the scope of the present invention.

41 Claims, No Drawings

ANTIBIOTIC COMPOSITIONS AND METHOD FOR USING SAME

BACKGROUND OF THE INVENTION

The present invention relates to antibiotic compositions and to methods for using such compositions. More particularly, the invention relates to antibiotic compositions which are effective in use and reduce the risks of harmful side effects, such as, irritation, on the body part, for example, the eye, being treated.

Various antibiotic components have been used in ocular applications, for example, to control or manage or prevent ocular infections and the like. Moreover, antibiotic components, such as tobramycin have been suggested for use in combination with other materials, such as ophthalmically acceptable non-steroidal anti-inflammatory drugs or NSAIDs. See, for example, Fu et al. U.S. Pat. No. 5,414,011, the disclosure of which is incorporated in its entirety herein by reference. Quinolones, such as ofloxacin, have been used in compositions for treating ocular infections. These antibiotic compositions include one or more additional components which act as preservatives, for example, benzalkonium chloride (BAK) or organomercurials.

However, the use of BAK, organomercurials or other preservative components may be problematic. For example, BAK may be incompatible with certain active components and organomercurials pose difficulties due to potential mercury toxicity, as well as poor chemical stability. Although these problems may be significant, a more pervasive and common concern caused by preservatives components is the tendency of such components to cause irritation, allergic reactions, and/or other detrimental side effects when the preserved composition is administered to a patient.

It would be advantageous to provide stable, effective antibiotic compositions, and methods for using such compositions, that provide reduced risks of irritation and/or other harmful side effects caused by preservatives typically present in such compositions.

SUMMARY OF THE INVENTION

New antibiotic compositions, for example, for use in mammalian eyes, preferably human eyes, and methods for using such compositions have been discovered. By administering present compositions to humans or animals, for example, to the eyes of humans or animals, desired therapeutic effects are provided, such as the prevention, control or management of ocular microbial infections, reductions in inflammation and/or pain and the like. Importantly, the present compositions are substantially is free of added or separate preservatives. This feature provides substantial benefits, for example, substantial elimination of irritation and/or other detrimental effects which may be caused by the presence of such added preservative components. The present compositions can be easily produced, for example, using conventional techniques and can be conveniently used, for example, employing conventional methods of administration.

In accordance with one aspect of the invention, the compositions comprise a quinolone component and a carrier component. The compositions are substantially free of other components effective as preservatives. The quinolone component is present in an amount effective as a antibiotic when the composition is placed in a mammalian eye. In one useful embodiment, the quinolone component in the composition has fungistatic activity. That is, the quinolone components in the present compositions may have sufficient anti-fungal properties or activity to substantially prevent increases in populations of fungi in such compositions. In effect, the present quinolone components may act as effective preservatives against fungal growth in the present compositions. The carrier component is present in an amount effective to act as a carrier for the quinolone component, and other active component or components, if present, in the composition, and preferably is ophthalmically acceptable.

In one very useful embodiment, the present compositions comprise a quinolone component, a non-steroidal anti-inflammatory drug (NSAID) component, and a carrier component effective to act as a carrier for the quinolone and NSAID components. The quinolone component is effective as an antibiotic, as described elsewhere herein. The NSAID component is present in an amount effective to reduce at least one of inflammation and pain when the composition is placed in a mammalian eye.

The present compositions preferably include a quinolone component which is halogenated, more preferably fluorinated. Very useful compositions and results are obtained when the quinolone component is an ofloxacin component.

Although any NSAID component may be used, the NSAID components included in the present compositions preferably are carboxylic (—COOH) group-containing NSAID components. More preferably, the NSAID component is a pyrrolo pyrrole component, still more preferably a ketorolac component.

The present carrier components may contain one or more pharmaceutically or ophthalmically acceptable ingredients, for example, tonicity adjuster components, buffer components, viscosity components, lubricity components, surfactant components and the like, conventionally used, for example, in ophthalmic formulations. Preferably, the compositions have pH's in the physiological range of human beings, for example, in the range of about 4 to about 8.5.

The present compositions may be in any form suitable for effective administration to the human or animal to be treated. Preferably, the compositions are present in a form selected from solutions, suspensions, gels, ointments solids and the like which are very effective for ocular administration. The carrier component may conveniently be selected and/or compounded to provide the composition in the form desired.

Methods of using these compositions are included in the scope of the present invention. Such methods comprise administering to a human or animal, preferably to a mammalian eye, a therapeutically effective amounts of the compositions as described herein. Such methods provide one or more benefits to the human or animal treated in accordance with the present methods. For example, such benefits include prevention, control or management of microbial infections, and reduction in inflammation and/or pain. Because the present compositions include no additional preservatives, the human or animal being treated is subjected to reduced risks of irritation and/or other detrimental or unpleasant side effects caused by the presence of such preservatives.

Any and all features described herein and combinations of such features are included within the scope of the present invention provided that the features of any such combination are not mutually inconsistent.

These and other aspects and advantages of the present invention are in the following detailed description and Examples and claims.

DETAILED DESCRIPTION

The present compositions comprise quinolone components and carrier components. Importantly, the present compositions are substantially free of other components effective as preservatives. Such substantially preservative-free compositions remain effective to provide the desired antibiotic effectiveness of the present compositions, while at the same time reducing the risk of irritation and/or other uncomfortable side effects caused by the presence of one or more added preservatives. Even though the present compositions are substantially preservative-free, it has been found that the present compositions have sufficient preservative efficacy to meet or exceed the standards of the United States Preservative Efficacy Test (USPET).

The present compositions include quinolone components. A number of such quinolone components are known and have been used for many years in antibiotic applications. For example, nalidixic acid has been available for the treatment of urinary tract infections. The useful quinolone components preferably are four-quinolones that contain a carboxylic moiety in the three position of the basic structure shown below:

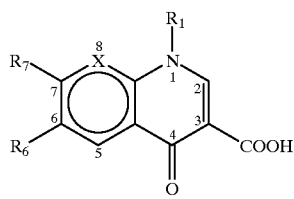

Preferably, the present quinolone components exhibit fungistatic properties in the present compositions. That is, the quinolone components in the present compositions preferably are effective to preserve the present composition against population growth of fungi, such as C. Albicans and A. niger.

The present quinolone components preferably are halogenated. For example, a chlorinated quinolone component, such as 9-chloro-3-methyl-10-(4-methyl-1-piperazinyl)-7-oxo-2,3-dihydro-7H-pyridol[1,2,3-de] [1,4]benzozaxine-6 carboxylic acid may be used.

More preferably, the present quinolone components are fluorinated. Examples of such fluorinated quinolones include norfloxacin, ciprofloxacin and ofloxacin. Such fluorinated quinolone components are highly effective against a range of bacteria and are useful in treating various microbial infections in the mammalian eye. Prior ofloxacin-containing compositions including such quinolone used for this purpose include additional preservatives, for example, BAK. Thus, while the quinolone is effective against the ocular infection, the preservatives present in such compositions may cause undesirable irritation and/or other disadvantageous side effects.

It has been found that the present quinolone components, such as ofloxacin, are very effective when present in compositions including substantially no additional components which are effective as preservatives. Moreover, quinolones, such as ofloxacin, have been found to have sufficient fungistatic activity to be useful in the present compositions to act as a preservative against fungal contamination. As noted previously, the present compositions including such quinolone components with no additional preservative components is sufficiently preserved so as to pass the USPET.

The present compositions include an antibiotically effective amount of the quinolone component. Such amounts may vary over a relatively broad range depending, for example, on the specific form of the composition being used, the specific quinolone component being used, the specific application for the composition, the frequency of use of the composition and the like factors. In many situations, the present compositions may include a quinolone component in an amount in a range of about 0.03% (w/v) or less to about 3% (w/v) or more. Preferably, the present compositions include the quinolone component in an amount in the range of about 0.15% (w/v) to about 0.5% (w/v) or about 1.1% (w/v).

The quinolone component may be any quinolone derivative which is acceptable or suitable for administration to the eye and has at least a portion, preferably a major portion or at least about 50% of the antibiotic effectiveness of the basic quinolone in the present composition in the mammalian eye. The present quinolone component may be selected from the quinolone itself or quinolone hydrates or ophthalmically acceptable salts of such quinolones, for example, including acid addition salts such as hydrochlorides, maleates, pamoates and the like, and alkali metal salts such as sodium and potassium salts, and mixtures thereof and the like.

The present carrier components may be selected from pharmaceutically acceptable organic and/or inorganic components which, preferably, in the present compositions are ophthalmically acceptable. As used herein, the term "ophthalmically acceptable" refers to a material which, at the concentration or amount in question, is compatible with ocular tissue, that is the material does not cause significant or undue detrimental effects when brought into contact with ocular tissue. The carrier component preferably is ophthalmically acceptable. Preferably, each component of the present compositions is also compatible with the other components of the compositions.

Examples of suitable materials useful in the present carrier components include water, mixtures of water and water-miscible solvents such as lower alkanols or aralkanols, vegetable oils, polyalkylene glycols, petroleum-based jelly, ethyl cellulose, ethyl oleate, carboxymethyl cellulose, polyvinylpyrrolidone, isopropyl mirstate, other conventionally employed pharmaceutically acceptable materials and the like.

The carrier component may also include auxiliary substances such as emulsifiers, wetting agents, bodying agents, buffer components, acids and/or bases, tonicity adjuster components, surfactant components, viscosity agents, lubricity components, other materials useful in ophthalmic formulations and the like.

Examples of optionally useful bodying agents include, but are not limited to, various polyethylene glycols, carbowaxes, petroleum jelly and the like.

Suitable buffers include, but are not limited to, inorganic buffers such as phosphate buffers, borate buffers and the like, and organic buffers, such as acetate buffers, citrate buffers, tromethamine and the like.

Tonicity adjusters optionally useful in the present compositions include, but are not limited to, dextrose, potassium chloride and/or sodium chloride and the like, is preferably sodium chloride.

Acids optionally useful in the present compositions include boric acid, hydrochloric acid, acetic acid, other acids which are ophthalmically acceptable in the concentrations used, and the like.

Bases which may be included in the present compositions include, but are not limited to, sodium and/or potassium hydroxides, other alkali and/or alkaline earth metal hydroxides, organic bases, other bases which are ophthalmically acceptable in the concentrations used, and the like.

The acid/bases/buffers preferably are included, if at all, to provide and/or maintain the present compositions at a pH in the physiologically acceptable range, more preferably in a range of about 4 to about 8.5, still more preferably about 6 to about 8, and especially about 6.8 to about 8.

Surfactant components optionally useful in the compositions of the present invention include, but are not limited to, lipoprotein detergents that when present in the compositions reduce the surface tension between the compositions and the eye (lacrimal) fluid. Preferably, nonionic surfactants are used.

Viscosity agents optionally useful in the compositions of the present invention include, but are not limited to, carbopol, cellulose derivatives such as hydroxypropylmethyl cellulose, sodium carboxymethyl cellulose, hydroxyethyl cellulose, other viscosity inducing materials useful in ophthalmic formulations and the like.

Lubricity components optionally useful in the compositions of the present invention include, but are not limited to, polyvinyl alcohol, polyvinylpyrrolidone, carbopol and the like.

The present compositions may include effective amounts of chelating or sequestering components, such as ethylene diamine tetraacetic acid (EDTA), citric acid, tartaric acid and the like. In one useful embodiment, the present compositions are substantially free of EDTA.

Other optional excipients useful in the present compositions include stabilizing agents such as antioxidants, for example, alkali metal metabisulfates, ascorbic acid and the like.

The carrier component may be in various forms. In one embodiment, the carrier component comprises a liquid, and the composition may be a solution or a suspension. In either situation, the carrier may simply contain water and one or more auxiliary components noted elsewhere herein.

The present compositions may be in any suitable form effective to be administered to the eye. Such forms include solutions, suspensions, ointments, gels, solids and the like. An ointment may be considered as a form intermediate between a suspension and a gel. Each of these forms of the present compositions can be prepared using techniques and processing which are conventional and well known in the art.

In another embodiment, the carrier component may be in the form of a clear material which forms a semi-solid "gel" at human body temperatures. Various polymers, many of which are conventional and well known in the art, can be included in the carrier components to provide the present compositions in the form of gels. For example, a polymer system including alkylene diamine tetra substituted with about 40% to about 80% poly(oxyethelene) units and about 20% to about 60% poly(oxypropylene) units may be employed. The molecular weight of the polymer used preferably is at least about 7,000 and can be as high as about 50,000, more preferably in the range of about 7,000 to about 30,000. The gel forming component, if any is present in an amount effective to provide the composition in the form of a gel. For example, such gel forming component may be present in an amount in a range of about 10% or less to about 50% or more by weight of the total carrier component.

The compositions may also be in the form of solid inserts, for example a solid dosage form that is suitable for insertion into the cul-de-sac of a mammalian eye. To this end, the composition components can be included with a non-bioerodible insert, for example, one which after dispensing the active component or components remains essentially intact, or a bio-erodible insert, for example, one that either is soluble in lacrimal fluids, or otherwise disintegrates.

A solid water soluble polymer may be employed in the carrier component. Such polymers include, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides, natural products such as gelatin, alginates, pectins, tragacanth, daraya, chondrus, agar, acacia; the starch derivatives such as starch acetate, hydroxyethyl starch ethers, hydroxypropy starch, as well as other synthetic derivatives such as polyvinyl alcohol, polyvinyl pyrrolidone, polyvinyl methyl ether, polyethylene oxide, neutralized carbopol and xanthan gum, mixtures thereof and the like.

In another useful embodiment, the present compositions further include a NSAID component, in addition to the quinolone component and the carrier component, in an amount effective to reduce inflammation and/or pain when the compositions are administered to a mammalian eye, for example, to prevent or treat diseases which are either caused by, associated with or accompanied by inflammatory processes and/or pain, including, among others, glaucoma, cystoid macular edema, uveitis, diabetic retinopathy and conjunctivitis, or any trauma caused by eye surgery or eye injury.

The NSAID component may or may not include a carboxylic (—COOH) group or moiety, or a carboxylic derived group or moiety. In one embodiment, the NSAID component inhibits the cyclo-oxygenase enzyme, which has two (2) isoforms, referred to as COX-1 and COX-2. Many of the well known NSAID components are basically non-selective COX inhibitors. NSAID components which are selective COX-2 inhibitors are also known. Both types of NSAID components, that is both non-selective COX inhibitors and selective COX-2 inhibitors are useful in accordance with the present invention. The NSAID component may be selected from phenylalkanoic acids, such as diclofenac, flurbiprofen, ketorolac, piroxicam and the like; indoles, such as indomethacin and the like; diarylpyrazoles, such as celecoxib and the like; pyrrolo pyrroles; and other agents that inhibit prostaglandin synthesis. A very useful NSAID component is the pyrrolo pyrrole which has a propionic acid moiety, known as ketorolac and derivatives thereof, such as non-toxic esters and salts thereof. Pyrrolo pyrroles have been suggested for use in the treatment of certain ophthalmic diseases in Waterbury U.S. Pat. No. 4,454,151, the disclosure of which is incorporated in its entirety herein by reference.

The NSAID component may be present in the present compositions in any suitable concentration effective to reduce inflammation or pain when the composition is placed in a mammalian eye. For example, the NSAID component, if present at all, preferably is present in an amount in a range of about 0.001% (w/v) or less to about 10% (w/v) or more, and more preferably in a range of about 0.02% (w/v) to about 0.5% (w/v) or about 1% (w/v).

The present compositions may be prepared using conventional techniques, for example, by formation of solutions, gels, suspensions, etc., using well known and conventional techniques. For a more detailed discussion of the preparation and administration of ophthalmic formulations see *Remingtons Pharmaceutical Sciences,* 15 Ed., Pgs. 1489 to 1504 (1975) which is incorporated in its entirety herein by reference.

In general, the present methods for treating mammalian eyes comprise administering to the mammalian eye a therapeutically effective amount of the present composition thereby providing an effective antibiotic in the mammalian eye, and, if NSAID component is present in the composition, thereby reducing inflammation or pain in the mammalian eye. The present methods of use may involve any suitable administration step or steps to provide an effective amount of the composition to the mammalian eye. Such administering may include, but is not limited to, topical application to the eye, instillation into the eye, placing an insert into the cul-de-sac (space) between the eyeball and the eyelid and the like. Other conventional methods of administering compositions to the eye may be employed provided that the present compositions are administered so as to provide the benefits desired.

The present use methods may be considered to be curative and/or preventative when applied, presurgically or immediately post traumatically, that is before a microbial infection develops, or before inflammation and/or pain is apparent. The present use methods are effective to reduce the risk of the formation of such infections and to reduce the severity of any inflammation or pain which may develop.

The dosage level of the present composition depends, of course, on many factors, for example, the particular application involved, the particular active component or components employed, the concentration of the active component or components in the composition, the severity of the infection/inflammation/pain and the individuals response to the treatment. Such dosage can be easily determined by routine and well known techniques to achieve the desired results in the individual patient being treated.

The following non-limiting examples illustrate certain aspects of the present invention.

EXAMPLES 1 TO 11

A series of compositions, Compositions 1 to 11, are prepared by blending various components together. These compositions have the following chemical make-ups.

Composition 1

| | |
|---|---|
| Ofloxacin | 0.6 w/v % |
| NaCl | 0.79 w/v % |
| pH | 6.4 |
| water | q.s. 100% |

Composition 2

| | |
|---|---|
| Ofloxacin | 1.0 w/v % |
| NaCl | 0.79 w/v % |
| pH | 6.4 |
| water | q.s. 100% |

Composition 3

| | |
|---|---|
| Ofloxacin | 0.6 w/v % |
| NaCl | 0.3 w/v % |
| EDTA | 0.1 wt % |
| Boric Acid | 1.0 w/v % |
| pH | 6.4 |
| water | q.s. 100% |

Composition 4

| | |
|---|---|
| Ofloxacin | 1.0 w/v % |
| NaCl | 0.3 w/v % |
| EDTA | 0.1 wt % |
| Boric Acid | 1.0 w/v % |
| pH | 6.4 |
| water | q.s. 100% |

Composition 5

| | |
|---|---|
| Ketorolac | 0.5 w/v % |
| Ofloxacin | 0.6 w/v % |
| NaCl | 0.79 w/v % |
| pH | 6.4 |
| water | q.s. 100% |

Composition 6

| | |
|---|---|
| Ketorolac | 0.5 w/v % |
| Ofloxacin | 1.0 w/v % |
| NaCl | 0.79 w/v % |
| pH | 6.4 |
| water | q.s. 100% |

Composition 7

| | |
|---|---|
| Ketorolac | 0.5 w/v% |
| Ofloxacin | 0.6 w/v % |
| NaCl | 0.3 w/v % |
| EDTA | 0.1 w/v % |
| Boric Acid | 1.0 w/v % |
| pH | 6.4 |
| water | q.s. 100% |

Composition 8

| | |
|---|---|
| Ketorolac | 0.5 w/v % |
| Ofloxacin | 1.0 w/v % |
| NaCl | 0.3 w/v % |
| EDTA | 0.1 w/v % |
| Boric Acid | 1.0 w/v % |
| pH | 6.4 |
| water | q.s. 100% |

Composition 9

| | |
|---|---|
| Ketorolac | 0.5 w/v % |
| Ofloxacin | 0.3 w/v % |
| NaCl | 0.79 w/v % |
| BAK | 0.005 w/v % |
| L-Arginine | 0.28 w/v % |
| pH | 6.4 |
| water | q.s. 100% |

Composition 10

| | |
|---|---|
| Ketorolac | 0.5 w/v % |
| Ofloxacin | 0.3 w/v % |
| NaCl | 0.79 w/v % |
| BAK | 0.005 w/v % |
| METHOCEL ®[(1)] | 0.1 w/v % |
| Carbopol[(2)] | 0.2 w/v % |
| pH | 6.4 |
| water | q.s. 100% |

Composition 11

| | |
|---|---|
| Ofloxacin | 0.3 w/v % |
| BAK | 0.005 w/v % |
| METHOCEL ®[(1)] | 0.1 w/v % |
| Carbopol[(2)] | 0.225 w/v % |
| Glycerine | 2.6 w/v % |
| pH | 6.5 |
| water | q.s. 100% |

[(1)]Methyl cellulose
[(2)]One of a series of polymers 2-propenoic acid cross-linked with alkyl ethers of pentaerythritol An abbreviated preservative efficacy test of each of these compositions is performed using *S. aureus* ATCC 6538 and *A. niger* ATCC 16404 as the test organisms. The compositions are tested against Ph Eur-A/B and USP criteria according to ARM T-005. Ten (10) milliliter of each composition is challenged with approximately $10^5$ cfu/ml of test organism. At the appropriate time intervals, the amount of bacterial and fungal survivors are assayed using Dey Engley broth (DE) as the neutralizer media. DE, along with filtration, is sufficient at neutralizing the antimicrobial agents in the compositions. One (1) ml of each sample is diluted into nine (9) ml of DE. One (1) of the 1:10 dilution is filtered through a 0.45 μm filter and washed with 100 ml saline/TWEEN® 80. After washing the filter a second time with 100 ml of a saline/TWEEN® 80 solution, the filtrate is placed onto a TSA plate for bacteria and SAB for fungi. The same procedure as stated above was followed for composition 11 (which is in the form of a gel) except a 1:100 dilution of the product is made prior to filtration (0.1 ml of product is added to 10 ml DE).

A summary of the results of these preservative efficacy tests is as follows:

| Composition | USP | Ph Eur-A | Ph Eur-B |
|---|---|---|---|
| 1 | PASS | FAIL | Marginal PASS |
| 2 | PASS | FAIL | FAIL |
| 3 | PASS | FAIL | Marginal PASS |
| 4 | PASS | FAIL | PASS |
| 5 | PASS | FAIL | FAIL |
| 6 | PASS | FAIL | FAIL |
| 7 | PASS | PASS | Marginal PASS |
| 8 | PASS | FAIL | PASS |
| 9 | PASS | PASS | PASS |
| 10 | PASS | PASS | PASS |
| 11 | PASS | PASS | PASS |

Detailed results of the preservative efficacy tests follows:

| Test Organism Inoculum level | Test Interval | Compositions | | | | | | | | | | |
|---|---|---|---|---|---|---|---|---|---|---|---|---|
| | | 1 | 2 | 3 | 4 | 5 | 6 | 7 | 8 | 9 | 10 | 11 |
| *S. aureus* ATTC 6538 $4 \times 10^5$ | 6 hours | $2 \times 10^5$ | $9 \times 10^4$ | $1 \times 10^5$ | $8 \times 10^4$ | $8 \times 10^4$ | $1 \times 10^5$ | $1 \times 10^5$ | $1 \times 10^5$ | <10 | <10 | <'0 |
| | 24 hours | $7 \times 10^4$ | $3 \times 10^4$ | $6 \times 10^4$ | <10 | $8 \times 10^3$ | $2 \times 10^3$ | $3 \times 10^3$ | $1 \times 10^4$ | <10 | <10 | <10 |
| | 7 days | <10 | <10 | <10 | $1 \times 10^1$ | <10 | <10 | <10 | <10 | <10 | <10 | <10 |
| | 14 days | <10 | <10 | <10 | <10 | <10 | <10 | <10 | <10 | <10 | <10 | <10 |
| | 28 days | <10 | <10 | <10 | <10 | <10 | <10 | <10 | <10 | <10 | <10 | <10 |
| *A. niger* ATCC 16404 $1 \times 10^5$ | 7 days | $8 \times 10^4$ | $8 \times 10^4$ | $4 \times 10^3$ | $1 \times 10^3$ | $7 \times 10^4$ | $7 \times 10^4$ | $2 \times 10^4$ | $3 \times 10^3$ | $1 \times 10^1$ | <10 | $1 \times 10^1$ |
| | 14 days | $2 \times 10^4$ | $3 \times 10^4$ | $2 \times 10^5$ | $1 \times 10^3$ | $9 \times 10^4$ | $9 \times 10^4$ | $2 \times 10^4$ | $7 \times 10^3$ | <10 | <10 | <10 |
| | 28 days | $1 \times 10^4$ | $3 \times 10^4$ | $2 \times 10^3$ | $8 \times 10^2$ | $2 \times 10^4$ | $1 \times 10^4$ | $4 \times 10^2$ | $1 \times 10^2$ | <10 | <10 | <1 |

The present compositions very effectively pass the USPET. In particular, the fact that Compositions 1 to 8, which include no component known to be effective as a preservative, pass the USPET is surprising, especially since prior art compositions which have included a quinolone, such as ofloxacin, have included preservatives, such as BAK. In addition, Compositions 1 to 8 do have sufficient antifungal activity to prevent *A. niger* from increasing in population. Thus, the quinolone, ofloxacin, included in these compositions has sufficient fungistatic activity to act as a preservative for the composition against *A. niger* contamination.

EXAMPLES 12 TO 23

A further series of compositions, Compositions 12 to 24, are prepared by blending various components together. These compositions have the following chemical make-ups. Each composition included sufficient water to total 100% by weight.

| EXAMPLE NO. | ACTIVES | CONCENTRATION, w/v % |
|---|---|---|
| 12 | Ketorolac | 0.5 |
|  | Ofloxacin | 0.3 |
|  | NaCl | 0.79 |
|  | pH | 6.4 |
| 13 | Ketorolac | 0.5 |
|  | Ofloxacin | 0.3 |
|  | NaCl | 0.30 |
|  | EDTA | 0.1 |
|  | Boric Acid | 1.0 |
|  | pH | 6.4 |
| 14 | Ketorolac | 0.5 |
|  | Ofloxacin | 0.3 |
|  | NaCl | 0.79 |
|  | BAK | 0.005 |
|  | pH | 6.4 |
| 15 | Ketorolac | 0.5 |
|  | Ofloxacin | 0.3 |
|  | NaCl | 0.79 |
|  | pH | 7.4 |
| 16 | Ketorolac | 0.5 |
|  | Ofloxacin | 0.3 |
|  | NaCl | 0.79 |
|  | BAK | 0.005 |
|  | pH | 7.6 |
| 17 | Ketorolac | 0.5 |
|  | Ofloxacin | 0.3 |
|  | NaCl | 0.79 |
|  | BAK | 0.005 |
|  | Octoxynol[3] | 0.007 |
|  | pH | 6.4 |
| 18 | Ketorolac | 0.5 |
|  | Ofloxacin | 0.3 |
|  | NaCl | 0.79 |
|  | BAK | 0.005 |
|  | Octoxynol[3] | 0.007 |
|  | pH | 7.6 |
| 19 | Ketorolac | 0.5 |
|  | Ofloxacin | 0.3 |
|  | NaCl | 0.79 |
|  | BAK | 0.005 |
|  | Cyclodextrin[4] | 0.1 |
|  | pH | 6.4 |
| 20 | Ketorolac | 0.5 |
|  | Ofloxacin | 0.3 |
|  | NaCl | 0.79 |
|  | BAK | 0.005 |
|  | Cyclodextrin[4] | 0.1 |
|  | pH | 7.6 |
| 21 | Ketorolac | 0.5 |
|  | Ofloxacin | 0.3 |
|  | NaCl | 0.79 |
|  | Purite[5] | 0.007 |
|  | pH | 7.6 |
| 22 | Ketorolac | 0.5 |
|  | Ofloxacin | 0.3 |
|  | NaCl | 0.79 |
|  | Purite[5] | 0.007 |
|  | Octoxynol[3] | 0.007 |
|  | pH | 7.6 |
| 23 | Ketorolac | 0.5 |
|  | Ofloxacin | 0.3 |
|  | NaCl | 0.79 |
|  | Purite[5] | 0.007 |
|  | Cyclodextrin[4] | 0.1 |
|  | pH | 7.6 |

[3] Polyethylene glycol mono (octylphenyl) ether
[4] 7-sulfobutylether beta-cyclodextrin
[5] Stabilized chlorine dioxide The samples were tested for preservative efficacy against Ph Eur-A/B and USP criteria according to ARM T-005. Ten (10) milliliters of each sample was challenged with approximately $10^5$ cfu/ml of test organism. The test organisms included *S. aureus* ATCC 6538, *P. aeruginosa* ATCC 9027, *E. coli* ATCC 8739, *C. albicans* ATCC 10231, and *A. niger* ATCC 16404. At the appropriate time intervals, the amount of bacterial and fungal survivors were assayed using DE as the neutralizer media. DE, along with filtration, is sufficient at neutralizing the antimicrobial agents in the compositions. One (1) ml of each sample was diluted into 9 ml of DE. The whole 10 ml was filtered through a 0.45 um filter and washed with 100 ml of phosphate buffered saline ph 5.4. After washing the filter a second time with 100 ml phosphate buffered saline/TWEEN® 80, the filter was placed onto a blood agar plate for bacteria and SAB for fungi.

The results are summarized in the below table.

| SAMPLE ID | USP | Ph Eur-A | Ph Eur-B |
|---|---|---|---|
| 12 | PASS | FAIL | FAIL |
| 13 | PASS | FAIL | FAIL |
| 14 | PASS | PASS | PASS |
| 15 | PASS | FAIL | FAIL |
| 16 | PASS | PASS | PASS |
| 17 | PASS | PASS | PASS |
| 18 | PASS | PASS | PASS |
| 19 | PASS | FAIL | PASS |
| 20 | PASS | PASS | PASS |
| 21 | PASS | FAIL | FAIL |
| 22 | PASS | FAIL | FAIL |
| 23 | PASS | FAIL | FAIL |

Detailed results of the preservation efficacy tests on Compositions 12 to 17 were as follows:

| Test Organism Inoculum level | Test Interval | Composition | | | | | |
|---|---|---|---|---|---|---|---|
| | | 12 | 13 | 14 | 15 | 16 | 17 |
| *S. aureus* ATCC 6538 $5 \times 10^5$ | 6 hours | $2 \times 10^5$ | $2 \times 10^5$ | 4 | $3 \times 10^5$ | <10 | 1 |
| | 24 hours | $2 \times 10^5$ | $2 \times 10^5$ | <10 | $3 \times 10^5$ | <10 | <10 |
| | 7 days | <10 | $2 \times 10^1$ | <10 | <10 | <10 | <10 |

-continued

| Test Organism Inoculum level | Test Interval | Composition 12 | 13 | 14 | 15 | 16 | 17 |
|---|---|---|---|---|---|---|---|
| | 14 days | <10 | <10 | <10 | <10 | <10 | <10 |
| | 28 days | <10 | <10 | <10 | <10 | <10 | <10 |
| P. aeruginosa | 6 hours | <10 | <10 | <10 | <10 | <10 | <10 |
| ATCC 9027 | 24 hours | <10 | <10 | <10 | <10 | <10 | <10 |
| $3 \times 10^5$ | 7 days | <10 | $2 \times 10^1$ | <10 | <10 | <10 | <10 |
| | 14 days | <10 | <10 | <10 | <10 | <10 | <10 |
| E. coli | 6 hours | $6 \times 10^1$ | $5 \times 10^1$ | <10 | $5 \times 10^1$ | <10 | <10 |
| ATCC 8739 | 24 hours | $5 \times 10^2$ | <10 | <10 | <10 | <10 | <10 |
| $5 \times 10^5$ | 7 days | <10 | <10 | <10 | <10 | <10 | <10 |
| | 14 days | <10 | <10 | <10 | <10 | <10 | <10 |
| | 28 days | <10 | <10 | <10 | <10 | <10 | <10 |
| C. albicans | 7 days | $1 \times 10^5$ | $2 \times 10^5$ | <10 | $3 \times 10^5$ | <10 | <10 |
| ATCC 10231 | 14 days | $1 \times 10^5$ | $2 \times 10^5$ | <10 | $1 \times 10^5$ | <10 | <10 |
| $3 \times 10^5$ | 28 days | $8 \times 10^4$ | $9 \times 10^4$ | <10 | $9 \times 10^4$ | <10 | <10 |
| A. niger | 7 days | $6 \times 10^4$ | $6 \times 10^4$ | $3 \times 10^1$ | $7 \times 10^4$ | <10 | $3 \times 10^1$ |
| ATCC 16404 | 14 days | $4 \times 10^4$ | $3 \times 10^4$ | 4 | $6 \times 10^4$ | $1 \times 10^2$ | <10 |
| $1 \times 10^5$ | 28 days | $3 \times 10^4$ | $3 \times 10^4$ | <10 | $4 \times 10^4$ | <10 | <10 |

Certain embodiments of the present compositions, that is Compositions 12 and 15, include no component known to be effective as a preservative. These compositions do, however, pass the USPET. In addition, although Compositions 12 and 15 do not pass the European Preservative Efficacy Tests, they do have sufficient antifungal activity to prevent C. albicans and A. niger from increasing in population. The quinolone, ofloxacin, included in these compositions has sufficient fungistatic activity to act as a preservative for the composition against C. albicans and A. niger contamination. Further, Compositions 21, 22 and 23 include stabilized chlorine dioxide which is known to be an effective preservative in ophthalmic formulations. However, such compositions also do not pass the European Preservative Efficacy Tests.

EXAMPLES 24 TO 33

Compositions 1 to 8, 12 and 15, in the form of solutions, are each administered to a human eye which has a microbial infection. Each composition is administered in an amount of about 1 to 2 drops per eye with the drops containing about 25 to 50 micro liters of the composition. The drops are administered 3 to 4 times per day.

After a week of such administering, each of the eyes treated is free of the microbial infection.

EXAMPLES 34 TO 39

Each of the Compositions 5 to 8, 12 and 15 are administered to an eye which has been subjected to surgical trauma. Before administration, each eye exhibits a degree of inflammation and is the source of a degree of pain.

Each composition is administered to the eye in an amount of about 1 to 2 drops per eye with the drops containing about 25 to 50 micro liters. The drops are administered 3 to 4 times per day.

After a week of such administering, each of the eyes treated exhibits no inflammation and is not a source of pain. In addition, each of the eyes has remained free of microbial infection.

While this invention has been described with respect to various specific examples and embodiments, it is to be understood that the invention is not limited thereto and that it can be variously practiced within the scope of the following claims.

What is claimed is:

1. A composition comprising:
    a quinolone component in an amount effective as an antibiotic when the composition is placed in a mammalian eye;
    a NSAID component in an amount effective to reduce inflammation or pain when the composition is placed in a mammalian eye; and
    a carrier component in an amount effective to act as a carrier for the quinolone component and the NSAID component in the composition, the carrier component being ophthalmically acceptable, the composition being free of other components effective as preservatives, the composition being sufficiently self-preserved so as to pass the United States Preservative Efficacy Test.

2. The composition of claim 1 wherein the NSAID component is a carboxyl group-containing NSAID component.

3. The composition of claim 1 wherein the carrier component is selected to provide the composition in a form selected from the group consisting of a solution, a suspension, a gel, an ointment and a solid.

4. The composition of claim 1 wherein the quinolone component is a halogenated quinolone component.

5. The composition of claim 4 wherein the NSAID component is a carboxyl group-containing NSAID component.

6. The composition of claim 1 wherein the quinolone component is a fluorinated quinolone component.

7. The composition of claim 6 wherein the NSAID component is a carboxyl group-containing NSAID component.

8. The composition of claim 1 wherein the quinolone component is an ofloxacin component.

9. The composition of claim 8 wherein the NSAID component is a carboxyl group-containing NSAID component.

10. The composition of claim 1 wherein the NSAID component is a ketorolac component.

11. The composition of claim 10 wherein the carrier component is selected to provide the composition in a form selected from the group consisting of a solution, a suspension, a gel and an ointment.

12. The composition of claim 10 wherein the quinolone component is a halogenated quinolone component.

13. The composition of claim 10 wherein the quinolone component is a fluorinated quinolone component.

14. The composition of claim 10 wherein the quinolone component is an ofloxacin component.

15. A method for treating a mammalian eye comprising:
administering to the mammalian eye a therapeutically effective amount of the composition of claim 1, thereby providing an effective antibiotic in the mammalian eye and reducing inflammation or pain in the mammalian eye.

16. A method for treating a mammalian eye comprising:
administering to the mammalian eye a therapeutically effective amount of the composition of claim 3, thereby providing an effective antibiotic in the mammalian eye and reducing inflammation or pain in the mammalian eye.

17. A method for treating a mammalian eye comprising:
administering to the mammalian eye a therapeutically effective amount of the composition of claim 4, thereby providing an effective antibiotic in the mammalian eye and reducing inflammation or pain in the mammalian eye.

18. A method for treating a mammalian eye comprising:
administering to the mammalian eye a therapeutically effective amount of the composition of claim 8, thereby providing an effective antibiotic in the mammalian eye and reducing inflammation or pain in the mammalian eye.

19. A method for treating a mammalian eye comprising:
administering to the mammalian eye a therapeutically effective amount of the composition of claim 10, thereby providing an effective antibiotic in the mammalian eye and reducing inflammation or pain in the mammalian eye.

20. A method for treating a mammalian eye comprising:
administering to the mammalian eye a therapeutically effective amount of the composition of claim 14, thereby providing an effective antibiotic in the mammalian eye and reducing inflammation or pain in the mammalian eye.

21. A composition comprising:
a quinolone component in an amount effective as an antibiotic when the composition is placed in a mammalian eye, the quinolone component in the composition having fungistatic activity; and
a carrier component in an amount effective to act as a carrier for the quinolone component in the composition, the component being ophthalmically acceptable, the composition being free of other components effective as preservatives, the composition being sufficiently self-preserved so as to pass the United States Preservative Efficacy Test.

22. The composition of claim 21 wherein the carrier component is selected to provide the composition in a form selected from the group consisting of a solution, a suspension, a gel, an ointment and a solid.

23. The composition of claim 21 wherein the quinolone component is a halogenated quinolone component.

24. The composition of claim 21 wherein the quinolone component is a fluorinated quinolone component.

25. The composition of claim 21 wherein the quinolone component is an ofloxacin component.

26. The composition of claim 21 which further comprises an additional active component in an amount effective to provide a therapeutic effect when the composition is placed in a mammalian eye, the carrier component being effective to act as a carrier for the additional active component.

27. The composition of claim 26 wherein the additional active component is a NSAID component in an amount effective to reduce inflammation or pain when the composition is placed in a mammalian eye.

28. The composition of claim 27 wherein the NSAID component is a carboxyl group containing NSAID component.

29. The composition of claim 27 wherein the NSAID component is a ketorolac component.

30. The composition of claim 29 wherein the quinolone component is an ofloxacin component.

31. A method for treating a mammalian eye comprising:
administering to the mammalian eye a therapeutically effective amount of the composition of claim 21.

32. A method for treating a mammalian eye comprising:
administering to the mammalian eye a therapeutically effective amount of the composition of claim 22.

33. A method for treating a mammalian eye comprising:
administering to the mammalian eye a therapeutically effective amount of the composition of claim 25.

34. A method for treating a mammalian eye comprising:
administering to the mammalian eye a therapeutically effective amount of the composition of claim 29.

35. A method for treating a mammalian eye comprising:
administering to the mammalian eye a therapeutically effective amount of the composition of claim 30.

36. The composition of claim 1 wherein the carrier component is selected to provide the composition as a solution.

37. The composition of claim 1 having a pH in a range of about 4 to 7.4.

38. The composition of claim 1 in a multi-dose format.

39. The composition of claim 21 wherein the carrier component is selected to provide the composition as a solution.

40. The composition of claim 21 having a pH in a range of about 4 to 7.4.

41. The composition of claim 21 in a multi-dose--dose format.

* * * * *